United States Patent [19]

Yotam et al.

[11] 4,157,711
[45] Jun. 12, 1979

[54] ELECTROCARDIOGRAPH APPARATUS CAPABLE OF DISCERNING THE H-WAVE IN THE P-Q INTERVAL

[75] Inventors: Reuben Yotam, Ramat Aviv; Yoram Lass, Tel Aviv; Abraham Caspi, Rehovot, all of Israel

[73] Assignee: Ramot University Authority for Applied Research & Industrial Development Ltd., Ramat Aviv, Israel

[21] Appl. No.: 890,240

[22] Filed: Mar. 27, 1978

[30] Foreign Application Priority Data

Apr. 1, 1977 [IL] Israel .................................. 51805

[51] Int. Cl.² ................................................ J61B 5/04
[52] U.S. Cl. ..................................... 128/708; 128/712
[58] Field of Search .................... 128/2.06 A, 2.06 B, 128/2.06 G, 2.06 R, 2.1 R

[56] References Cited

U.S. PATENT DOCUMENTS

| | | | |
|---|---|---|---|
| 3,557,354 | 1/1971 | Trimble | 128/2.1 R |
| 3,654,916 | 4/1972 | Neilson | 128/2.06 A |
| 3,809,071 | 5/1974 | Davolos et al. | 128/2.06 B |

OTHER PUBLICATIONS

Flowers et al., "American Journal of Cardiology" vol. 33, No. 3, Mar. 1974, pp. 384–389.

*Primary Examiner*—William E. Kamm
*Attorney, Agent, or Firm*—Benjamin J. Barish

[57] ABSTRACT

Electrocardiograph apparatus capable of discerning the H-wave in the P-Q interval of an ECG signal comprises a charge transfer device delaying the ECG signal and a signal averager circuit triggerable by an R-wave peak detector for summing a plurality of the delayed ECG signals in time-locked relationship to the detected R-wave peak.

3 Claims, 5 Drawing Figures

ELECTROCARDIOGRAPH APPARATUS CAPABLE OF DISCERNING THE H-WAVE IN THE P-Q INTERVAL

BACKGROUND OF THE INVENTION

The present invention relates to electrocardiograph apparatus, and particularly to such apparatus including a system for processing an ECG electrical signal to enable discerning the H-wave in the P-Q interval produced by the HIS-bundle.

ECG's (electrocardiograms) are electrical potential traces, or signal waveforms, accompanied by the contractions of the different cavities of the heart. They are an important aid in the study and diagnosis of abnormal heart activity. A typical ECG signal, produced by placing electrodes against the patient's skin, includes P-, Q-, R-, S- and T-waves which are all easily discernable and thereby aid in diagnosing certain aspects of the heart condition. Another wave, also extremely helpful in diagnosing other aspects of the heart condition, is the H-wave in the P-Q interval produced by the HIS-bundle, it being generally recognized that a prolongation in the H-Q interval is strong evidence of an impending complete heart block. However, the H-wave is so weak, compared to surrounding noise, that it is not discernible in a normal ECG taken by the use of skin electrodes, even when the ECG is amplified by conventional means. Accordingly, in order to discern the H-wave, particularly the H-Q interval, the present procedure is to insert one of the electrodes into the heart itself by means of a catheter. Needless to say, such an invasive procedure is far from satisfactory, since it involves a significant element of danger, is time-consuming, and requires costly equipment. For this reason, H-wave electrocardiography is applied only in a very small number of cases compared to general electrocardiography, thereby depriving many patients of the benefits of this important diagnostic aid.

Several systems have been proposed for the non-invasive discernment of the H-wave in an ECG signal. One proposed technique uses a computer which continuously samples the ECG signal in a ring buffer fashion, and upon interupt, the P-R segment is extracted from the ring buffer and is added to the current average for that segment. This technique, however, requires costly computer equipment and elaborate computer-programming procedures, and is therefore not satisfactory for general practice. Another technique proposed is to record the ECG signal on magnetic tape and then to play the tape in reverse so as to obtain the averages between ORS complexes and P-waves without using a large computer. However, such a system also involves special equipment, procedures, and skills and is therefore also not satisfactory for general practice.

An object of the present invention is to provide electrocardiograph apparatus with a system which is capable of discerning the H-wave and yet which is of low cost and simple operation soas to be suitable for general practice.

BRIEF SUMMARY OF THE INVENTION

According to the present invention, there is provided a system for use in processing ECG electrical signals to enable discerning the H-wave, which system comprises a charge transfer device capable of delaying the ECG signal at least 50 ms, preferably at least 200 ms, and a signal averager circuit triggered by an R-wave peak detector for summing a plurality of the delayed ECG signals in time-locked relationship to the detected R-wave peak.

Preferably, the charge transfer device delays the ECG signals at least 200 ms, this being the time interval the R-wave follows the leading edge of the ECG signal. Especially good results have been produced by using charge transfer devices of the integrated circuit bucket-brigade type.

The use of a processing system including such charge transfer device has greatly simplified the elaborate hardware heretofore used and has enabled all the necessary circuitry to be incorporated into a portable ECG recorder. Thus, the invention permits conventional, (e.g., portable), ECG recorder apparatus used for general practice to be provided with the additional option of discerning the H-wave in the P-Q interval.

BRIEF DESCRIPTION OF THE DRAWINGS

The invention is herein described, by way of example only, with reference to the accompanying drawings, wherein.

DESCRIPTION OF THE PREFERRED EMBODIMENT

Figure 1:
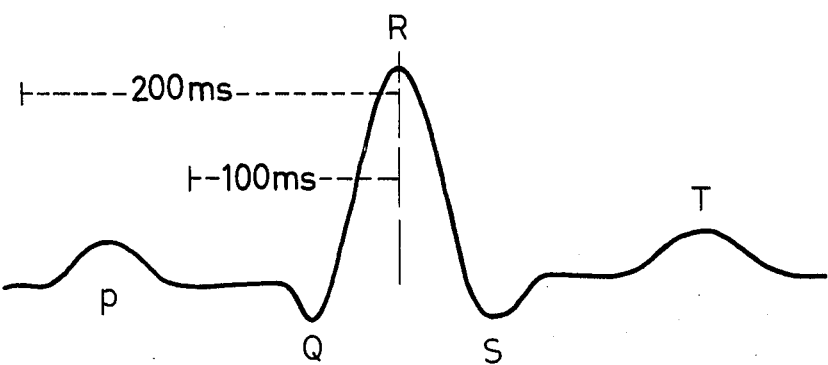
FIG. 1 illustrates an idealized ECG electrical signal wave-form, showing its various peaks or waves which are helpful in diagnosing the condition of the heart.

With reference first to FIG. 1, there is shown an idealized ECG signal produced by conventional ECG techniques wherein electrodes are placed against the skin of the patient to detect the electrical potential traces accompanying the contractions of the different cavities of the heart. In a typical ECG signal, the principal, and easily discernible, waves are the P-, Q-, R-, S-, and T-waves, as shown in FIG. 1. It will be noted in FIG. 1 that the peak of the R-wave occurs about 200 ms (millesecends) following the leading edge of the ECG signal waveform, the P-wave (a relatively long wave) ending about 100 ms preceding the peak of the R-wave. The H-wave, produced by the HIS-bundle in the heart, is not seen in FIG. 1 since, as indicated above, it is so weak in comparison to the background noise as not to be discernible in the usual ECG. The H-wave, however, occurs between the P-wave and the Q-wave (See FIGS. 4 and 5), about 50 ms preceding the R-wave peak; as indicated above, any prolongation between its occurrence and the occurrence of the Q-wave is generally recognized as strong evidence of an impending complete heart block.

Figure 2:
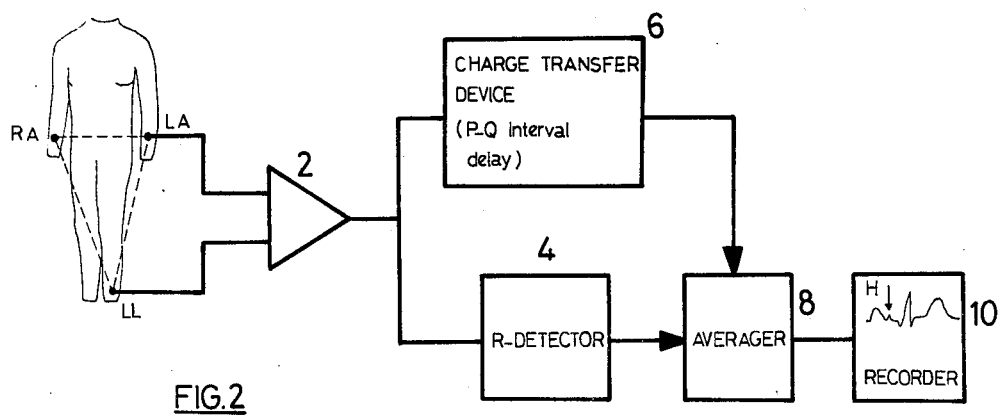
FIG. 2 is a block diagram illustrating one form of electrocardiograph apparatus constructed in accordance with the present invention.
Figure 3:
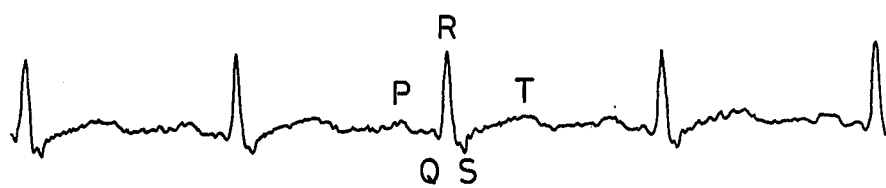
FIG. 3 illustrates a typical ECG signal waveform before the signal is processed in accordance with the present invention.

Apparatus for producing the ECG in accordance with the invention is illustrated in FIG. 2. It includes the conventional skin electrodes, namely a right-arm electrode RA, a left-arm electrode LA, and a left-leg electrode LL, which are placed in contact with the patient's skin at these locations to sense the electrical potentials accompanying the contractions of the heart cavities and to produce the ECG signal waveform. A conventional ground electrode (not shown) is normally also provided. The apparatus further includes the conventional amplifier 2 for amplifying the ECG signal waveform.

The apparatus of FIG. 2 further includes the following additional circuits which act, in the manner described below, to increase the signal-to-noise ratio of the ECG signal outputted from amplifier 2 in order to enable discernment of the H-wave produced by the HIS-bundle; a peak detector 4 which detects the R-wave peak, occurring about 200 ms following the leading edge of the ECG signal; a charge transfer device 6, which delays the ECG outputted from amplifier 2 for at least the above time interval of 200 ms; and a signal averager circuit 8 triggerable by the R-wave peaks outputted from peak detector 4 for summing a plurality of the delayed ECG signals from the charge transfer device 6 in time-locked relationship to the R-wave peaks. The output of the signal averager 8 is fed to an output unit 10, which may be a recorder for recording the signal on a record medium, and/or a display device, such as a CRT, for displaying the outputted signal.

The signal averager circuit 8 is one of the known types of circuits, such as special-purpose digital computers, capable of isolating and evaluating small electrical responses masked by random background noise. Such circuits are commonly used on-line providing a real-time reinforcement of the desired electrical signal. They usually operate according to a summation (averaging) technique which is automatically programmed to time-lock the desired signal with respect to a known stimulus or reference pulse and to sum successive responses. As a result, the signal under investigation sums in phase and is therefore added arithmetically, whereas the random background noise sums out of phase and therefore tneds to cancel out. It can be shown that the improvement in the signal-to-noise ratio is proportional to the square root of the number of times the signal is summed in the averager circuit. Thus, if the signal is summed 64 times, the signal-to-noise ratio will be improved by a factor of 8.

In the system illustrated in FIG. 2, the signal averager circuit 8 is triggered by the R-wave peaks from the peak detector 4, and is fed with the ECG signal after the latter has been delayed by the charge transfer device 6 by at least 200 ms. As indicated above, 200 ms is the period of time in which the R-wave peak occurs following the leading edge of the ECG signal. Preferably the delay is longer than 200 ms, e.g., 300 ms. The averager operates for periods of 400 ms; or more.

It will thus be seen that the average circuit 8 does not average the ECG signal in real time, but rather averages it in delayed time. In other words, the system illustrated in FIG. 2 enables the average circuit 8 to be triggered by a peak (the R-wave peak from the detector 4) in the electrical signal being processed, and acts to reinforce not only the portion of the signal occurring after the triggering peak, but also the portion occurring before the triggering peak, namely from the leaking edge of the ECG signal to the R-Wave peak. Accordingly, the complete successive ECG signals are summed in phase-locked relationship to the R-wave peak to thereby arithmetically add or sum the ECG signal in phase, while the random background noise is summed out of phase and thereby tends to cancel out.

Figure 4:
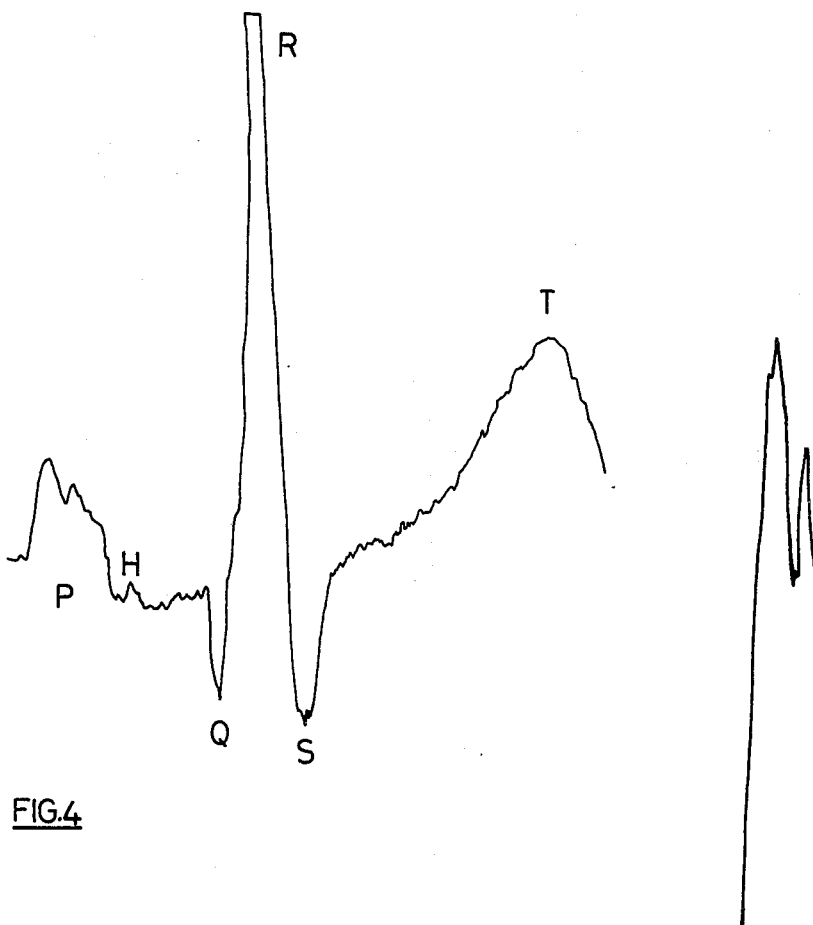
FIG. 4 illustrates a portion of an ECG signal after it has been processed and amplified in accordance with the present invention.
Figure 5:
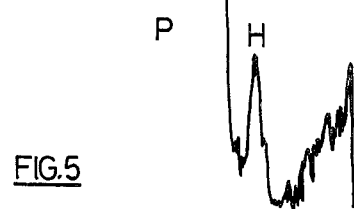
FIG. 5 illustrates a fragment of the ECG signal of FIG. 4 after it has been further processed.

FIG. 4 illustrates the portion of the ECG signal between the P-wave and T-wave after being summed a number of times, wherein it will be seen that the H-wave is discernible between the P- and Q-peaks. FIG. 5 illustrates the portion between the P- and Q-peaks after being summed a greater number of times, wherein it will be seen that the H-wave is even more pronounced.

The charge transfer device 6 is preferably an integrated circuit plural-stage bucket-brigade line device, for example Reticon SAD-1024, or Philips TDA 1022, including an amplifier. The former (Reticon) device is commercially available today with delays up to about 500 ms; the latter (Philips) device is commercially available with delays up to about 50 ms, and therefore a plurality of such devices may be used in series. As pointed out above, the use of a charge transfer device for effecting the delay substantially simplifies the equipment and enables all the necessary circuitry to be incorporated into a portable ECG recorder. Thus, conventional ECG recorders can be provided, at relatively low additional costs, with the capability of discerning the H-wave in the P-Q internal.

The signal averager circuit 8 may be one of the many commercially available units, for example Intel Model 8080 microprocessor, Ortec Signal Averager 4620/4623, Mnemotron Computer of Average Transients (CAT), or Digital Equipment Corporation Lab 8 Signal Averager; and the peak detector 4 may be a conventional Schmidt Trigger.

Preferably, the ECG signal is delayed at least 200 ms (e.g. 300 ms) before being inputted into the signal averager circuit 8, as described above, since this results in the complete ECG signal being reinforced, starting from its leading edge. However, in some cases it may be desirable to reinforce only the portion of the ECG signal showing the P-Q interval, to discern only whether there is an H-Q prolongation. In such cases, the delay can be 50 ms which is the time interval between the occurrence of the H-wave and the peak of the R-wave, or 100 ms, which is the time interval between the end of the P-wave and the peak of the R-wave.

Many other variations, modifications, and applications of the invention may be made.

What is claimed is:

1. Electrocardiograph apparatus, comprising: electrode means for application to external parts of a patient to produce ECG signals accompanying the contractions of the different cavities of the heart; a system for processing the ECG electrical signals to enable discerning the H-wave produced by the HIS-bundle, comprising: an R-wave peak detector for detecting the peak of the R-wave in the ECG signal; a charge transfer device for delaying the ECG signal at least 50 ms; a signal averager circuit triggerable by a trigger pulse for summing a plurality of the ECG signals in time-locked relationship to the trigger pulse; means for inputting said delayed ECG signal into the signal averager circuit; means for triggering the signal averager circuit by said detected R-wave peak, thereby causing the signal averager circuit to sum a plurality of the ECG signals in time-locked relationship to the detected R-wave peak; and display means for displaying the output of said signal averager circuit.

2. The apparatus according to claim 1, wherein said charge transfer device delays the ECG signal at least 200 ms, this being the time interval the R-wave follows the leading edge of the ECG signal.

3. Apparatus according to claim 1, further including a recording device for recording the output of said signal averager circuit.

* * * * *